United States Patent
Baty et al.

(10) Patent No.: US 10,174,117 B2
(45) Date of Patent: Jan. 8, 2019

(54) ANTI-HER2 SINGLE DOMAIN ANTIBODIES, POLYPEPTIDES COMPRISING THEREOF AND THEIR USE FOR TREATING CANCER

(71) Applicants: INSERM (INSTITUT NATIONAL DE LA SANTE ET DE LA RECHERCHE MEDICALE), Paris (FR); CENTRE NATIONAL DE LA RECHERCHE SCIENTIFIQUE (CNRS), Paris (FR); UNIVERSITE D'AIX MARSEILLE, Marseilles (FR); INSTITUT JEAN PAOLI & IRENE CALMETTES, Marseilles (FR)

(72) Inventors: Daniel Baty, Marseilles (FR); Patrick Chames, Marseilles (FR); Brigitte Kerfelec, Marseilles (FR); Marc Turini, Marseilles (FR)

(73) Assignees: INSERM (INSTITUT NATIONAL DE LA SANTE ET DE LA RECHERCHE MEDICALE), Paris (FR); CENTRE NATIONAL DE LA RECHERCHE SCIENTIFIQUE (CNRS), Paris (FR); UNIVERSITE D'AIX MARSEILLE, Marseilles (FR); INSTITUT JEAN PAOLI & IRENE CALMETTES, Marseilles (FR)

( * ) Notice: Subject to any disclaimer, the term of this patent is extended or adjusted under 35 U.S.C. 154(b) by 0 days.

(21) Appl. No.: 14/897,122

(22) PCT Filed: Jun. 11, 2014

(86) PCT No.: PCT/EP2014/062075
§ 371 (c)(1),
(2) Date: Dec. 9, 2015

(87) PCT Pub. No.: WO2014/198748
PCT Pub. Date: Dec. 18, 2014

(65) Prior Publication Data
US 2016/0122432 A1    May 5, 2016

(30) Foreign Application Priority Data

Jun. 11, 2013   (EP) .................................... 13305791

(51) Int. Cl.
*C07K 16/32*    (2006.01)
*C07K 16/28*    (2006.01)
*A61K 39/00*    (2006.01)

(52) U.S. Cl.
CPC ........ *C07K 16/2863* (2013.01); *C07K 16/283* (2013.01); *C07K 16/32* (2013.01); *A61K 2039/505* (2013.01); *C07K 2317/22* (2013.01); *C07K 2317/24* (2013.01); *C07K 2317/31* (2013.01); *C07K 2317/55* (2013.01); *C07K 2317/565* (2013.01); *C07K 2317/569* (2013.01); *C07K 2317/62* (2013.01); *C07K 2317/73* (2013.01); *C07K 2317/92* (2013.01)

(58) Field of Classification Search
CPC ................ C07K 16/32; C07K 2317/31; C07K 2317/569; C07K 2317/62; C07K 2317/565
USPC ..................................... 424/135.1; 530/387.3
See application file for complete search history.

(56) References Cited

U.S. PATENT DOCUMENTS

2016/0280795 A1* 9/2016 Wang ................. C07K 16/2809

FOREIGN PATENT DOCUMENTS

WO    WO 2004/003019    *  6/2004
WO    2012/089814 A1    7/2012

OTHER PUBLICATIONS

Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Turini et al. Oncotarget, vol. 5, No. 14: 5304-5319.*
Rakovich et al. SCCSNano vol. 8, No. 6, 5682-5695 (2014).*
*Amgen v Sanofi and Regeneron* (Case: 17-1480 Document: 176 Filed: Feb. 6, 2018).*
Sircar et al. (J Immunol. Jun. 1, 2011;186(11):6357-67. doi: 10.4049/jimmunol. 1100116. Epub Apr. 27, 2011).*
Even-Desrumeaux et al., "Single-domain antibodies: a versatile and rich source of binders for breast cancer diagnostic approaches", Molecular Biosystems, Sep. 1, 2012, pp. 2385-2394, vol. 8, No. 9, Royal Society of Chemistry, GB.
"Lama glama anti-HER2 single domain antibody C7b mRNA, partial cds", Database ENA, Feb. 27, 2013, Web.
Chames et al., "Bispecific antibodies for cancer therapy: the light at the end of the tunnel?", MABS, Nov. 1, 2009, pp. 539-547, vol. 1, No. 6, Landes Bioscience, US.
Shahied et al., "Bispecific minibodies targeting HER2/neu and CD16 exhibit improved tumor lysis when placed in a divalent tumor antigen binding format", Journal of Biological Chemistry, Dec. 24, 2004, pp. 53907-53914, vol. 279, No. 52, American Society for Biochemistry and Molecular Biology.
Chames et al., "Therapeutic antibodies: successes, limitations, and hopes for the future", British Journal of Pharmacology, May 2009, pp. 220-233, vol. 157, No. 2.

(Continued)

*Primary Examiner* — Lynn A Bristol
(74) *Attorney, Agent, or Firm* — Whitham & Cook, P.C.

(57) ABSTRACT

The present invention relates to anti-HER2 single domain antibodies, polypeptides comprising thereof and their use for treating cancer.

Figure 1:
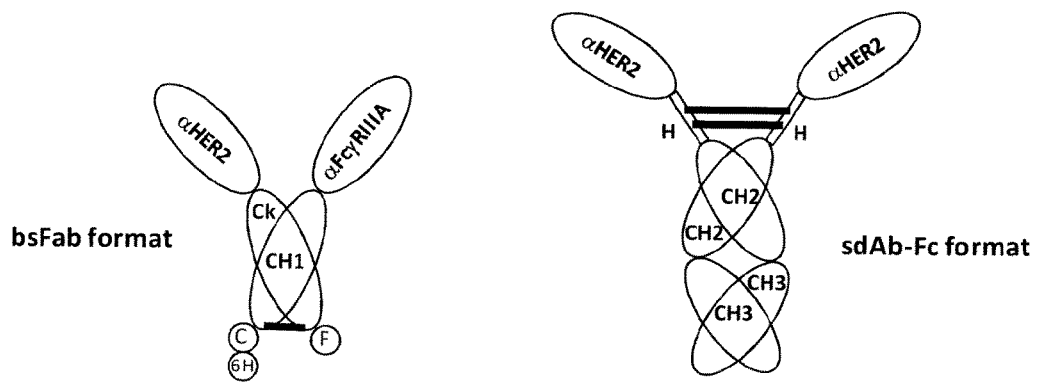

16 Claims, 4 Drawing Sheets
Specification includes a Sequence Listing.

(56) References Cited

OTHER PUBLICATIONS

Klervi et al., "Strong and oriented immobilization of single domain antibodies from crude bacterial lysates for high-throughput compatible cost-effective antibody array generation", Molecular Biosystems, Nov. 1, 2010, pp. 2241-2248, vol. 6, No. 11, Royal Society of Chemistry, GB.
Gruel et al., "Bypassing Tumor-Specific and Bispecific Antibodies: Triggering of Antitumor Immunity by Expression of Anti-FCgammar SCFV on Cancer Cell Surface", Gene Therapy, Nov. 1, 2001, pp. 1721-1728, vol. 8, No. 22.
Holt, Lucy J., et al. "Domain antibodies: proteins for therapy." Trends in biotechnology 21.11 (2003): 484-490.†

\* cited by examiner
† cited by third party

Clones C7B anti-HER2 Alignement IMGT

```
              /       FR1        /     CDR1     /       FR2       /   CDR2   /               FR3                 /       CDR3          /    FR4
              1        10        20        30        40        50        60        70        80        90        100       110       120
              123456789012345678901234567890123456789012345678901234567890123456789012345678901234567890123456789012345678901234567890
C7B     QVQLVQSGG.GLVQASGGSLRLSCAAS GRTF....SSYA MAWFRQAPGKEREFVAA ISWS..GANI YYADSVK.GRFTISRDNAKDTVYLQMNSLKPEDTAVYYC AVKLGFAP...VEERQYDY WGQGTQVTVSS
Human   EVQLVESGG.GLVQPGGSLRLSCAAS GFTF....SSYA MSWVRQAPGKGLEWVSA ISGS..GGST YYADSVK.GRFTISRDNSKNTLYLQMNSLRAEDTAVYYC AK..........FYFDY WGQGTLVTVSS
Mut     E         P                                    S V           GL W S                        Y           S N L              RA
```

Human V domain : AJ879486 Homsap IGHV3-23*04 F
EVQLVESGG.GLVQPGGSLRLSCAAS GFTF....SSYA MSWVRQAPGKGLEWVSA ISGS..GGST YYADSVK.GRFTISRDNSKNTLYLQMNSLRAEDTAVYYC AK Human J domain : J00256  Homsap IGHJ4*01
FYFDYWGQGTLVTVSS

Figure 6

SEQUENCE LISTING

```
<160> NUMBER OF SEQ ID NOS: 14

<210> SEQ ID NO 1
<211> LENGTH: 7
<212> TYPE: PRT
<213> ORGANISM: Artificial
<220> FEATURE:
<223> OTHER INFORMATION: Synthetic CDR1

<400> SEQUENCE: 1

Arg Thr Phe Ser Ser Tyr Ala
1               5

<210> SEQ ID NO 2
<211> LENGTH: 7
<212> TYPE: PRT
<213> ORGANISM: Artificial
<220> FEATURE:
<223> OTHER INFORMATION: Synthetic CDR2
```

<400> SEQUENCE: 2

Ile Ser Trp Ser Gly Ala Asn
1               5

<210> SEQ ID NO 3
<211> LENGTH: 16
<212> TYPE: PRT
<213> ORGANISM: Artificial
<220> FEATURE:
<223> OTHER INFORMATION: Synthetic CDR3

<400> SEQUENCE: 3

Ala Val Lys Leu Gly Phe Ala Pro Val Glu Glu Arg Gln Tyr Asp Tyr
1               5                   10                  15

<210> SEQ ID NO 4
<211> LENGTH: 123
<212> TYPE: PRT
<213> ORGANISM: Artificial
<220> FEATURE:
<223> OTHER INFORMATION: Synthetic C7B

<400> SEQUENCE: 4

Gln Val Gln Leu Val Gln Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Ala Trp Phe Arg Gln Ala Pro Gly Lys Glu Arg Glu Phe Val
        35                  40                  45

Ala Ala Ile Ser Trp Ser Gly Ala Asn Ile Tyr Val Ala Asp Ser Val
    50                  55                  60

Lys Gly Arg Phe Thr Ile Ser Arg Asp Asn Ala Lys Asp Thr Val Tyr
65                  70                  75                  80

Leu Gln Met Asn Ser Leu Lys Pro Glu Asp Thr Ala Val Tyr Tyr Cys
                85                  90                  95

Ala Val Lys Leu Gly Phe Ala Pro Val Glu Glu Arg Gln Tyr Asp Tyr
            100                 105                 110

Trp Gly Gln Gly Thr Gln Val Thr Val Ser Ser
        115                 120

<210> SEQ ID NO 5
<211> LENGTH: 57
<212> TYPE: DNA
<213> ORGANISM: Artificial
<220> FEATURE:
<223> OTHER INFORMATION: Synthetic primer

<400> SEQUENCE: 5
catgccatga ctcgcggccc agccggccat ggcccaggtg cagctggtgc agtctgg    57

<210> SEQ ID NO 6
<211> LENGTH: 57
<212> TYPE: DNA
<213> ORGANISM: Artificial
<220> FEATURE:
<223> OTHER INFORMATION: Synthetic primer

<400> SEQUENCE: 6
catgccatga ctcgcggccc agccggccat ggcccaggtc accttgaagg agtctgg    57

<210> SEQ ID NO 7
<211> LENGTH: 57

<212> TYPE: DNA
<213> ORGANISM: Artificial
<220> FEATURE:
<223> OTHER INFORMATION: Synthetic primer

<400> SEQUENCE: 7
catgccatga ctcgcggccc agccggccat ggccgaggtg cagctggtgg agtctgg          57

<210> SEQ ID NO 8
<211> LENGTH: 57
<212> TYPE: DNA
<213> ORGANISM: Artificial
<220> FEATURE:
<223> OTHER INFORMATION: Synthetic primer

<400> SEQUENCE: 8
catgccatga ctcgcggccc agccggccat ggcccaggtg cagctgcagg agtcggg          57

<210> SEQ ID NO 9
<211> LENGTH: 41
<212> TYPE: DNA
<213> ORGANISM: Artificial
<220> FEATURE:
<223> OTHER INFORMATION: Synthetic primer

<400> SEQUENCE: 9
ccacgattct gcggccgctg aggagacrgt gacctgggtc c                            41

<210> SEQ ID NO 10
<211> LENGTH: 36
<212> TYPE: DNA
<213> ORGANISM: Artificial
<220> FEATURE:
<223> OTHER INFORMATION: Synthetic primer

<400> SEQUENCE: 10
tggtgcagcc accgtacgtg aggagacggt gacctg                                  36

<210> SEQ ID NO 11
<211> LENGTH: 59
<212> TYPE: DNA
<213> ORGANISM: Artificial
<220> FEATURE:
<223> OTHER INFORMATION: Synthetic primer

<400> SEQUENCE: 11
cagctgggtt attattgctc gctgcgcagc cggccatggc cgaggtgcag ctggtgcag         59

<210> SEQ ID NO 12
<211> LENGTH: 62
<212> TYPE: DNA
<213> ORGANISM: Artificial
<220> FEATURE:
<223> OTHER INFORMATION: Synthetic primer

<400> SEQUENCE: 12
acaggaaaca gaattccata tgaaatacct attaccaaca gcagcagctg ggttattatt        60
gc                                                                       62

<210> SEQ ID NO 13
<211> LENGTH: 98
<212> TYPE: PRT
<213> ORGANISM: Homo sapiens

<400> SEQUENCE: 13

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 14
<211> LENGTH: 16
<212> TYPE: PRT
<213> ORGANISM: Homo sapiens

<400> SEQUENCE: 14

Phe Tyr Phe Asp Tyr Trp Gly Gln Gly Thr Leu Val Thr Val Ser Ser
1               5                   10                  15
```

ANTI-HER2 SINGLE DOMAIN ANTIBODIES, POLYPEPTIDES COMPRISING THEREOF AND THEIR USE FOR TREATING CANCER

FIELD OF THE INVENTION

The present relates to Anti-HER2 single domain antibodies and their use for treating cancer

BACKGROUND OF THE INVENTION

Breast cancer is one of the most common malignant tumors in women. More than one million new cases of breast cancer occur worldwide annually, and nearly 400 thousand people died from breast cancer every year. In recent years, the incidence of breast cancer showed a clear upward trend in the world. Despite in high and low endemic areas, the incidence of breast cancer increases by 5-20%. The common treatments for breast cancer include surgery, chemicotherapy and endocrine therapy and so on. Although these conventional treatments may prolong survival in patients to a large extent, their side effects are serious and their therapeutic effect is hard to be further improved. Targeted cancer therapy is a new treatment for cancer that has arisen in recent years, of which the representative is antitumor monoclonal antibody. HER2 (human epidermal growth factor receptor 2) is a transmembrane protein with tyrosine kinase activity, having a molecular weight of about 185 KD. Anti-HER2 humanized monoclonal antibody may specifically bind to HER2, and has antitumor mechanisms as follows: specifically binding to the extracellular domain of HER2 receptor to block the constitutive activation of HER2 homodimers and interfere the heterodimer formation of HER2 with other ErbB family members; mediating the endocytosis and the degradation in lysosomes of HER2 receptor; activating PTEN (phosphatase and tensin homology) and blocking PI3K (Phosphatidylinositol 3-kinase) signal channel; inhibiting tumor cell proliferation by regulation of cell cycle; promoting tumor cell apoptosis; inhibiting tumor angiogenesis; ADCC (antibody-dependent cell-mediated cytotoxicity) effect; inhibiting DNA repair; increasing the cytotoxicity of chemotherapeutic agents; reversing the resistance of tumor cells to the killing effects of host cell factors, and etc. (Pergram M, Ngo D, Application and potential limitations of animal models utilized in the development of trastuzumab (Herceptin®): A case study. Adv Drug Deliv Rev. 2006; 58:723-34 Anti-HER2 humanized monoclonal antibody (e.g. Trastuzumab, trade name: Herceptin) has been used in clinical trials to treat patients with HER2 overexpressing metastatic breast cancer as single drug, who had received but failed one or more chemotherapy regimens for their metastases. Response rates to single-agent trastuzumab range from 12 to 34% for metastatic breast cancer and significant improvements in survival rates are achieved in patients with early-stage HER2-overexpressing breast cancer in the adjuvant setting. However patients with a low expression of HER2 (i.e. HER2+ or HER2++ patients) are not eligible for a treatment with an anti-HER2 humanized monoclonal antibody such as Trastuzumab. Accordingly, there is a need for the treatment of patient having a cancer with a HER2 low expression.

SUMMARY OF THE INVENTION

The present invention relates to anti-HER2 single domain antibodies, and polypeptides comprising thereof.

DETAILED DESCRIPTION OF THE INVENTION

Trastuzumab is now established for the treatment of HER2$^{high}$ metastatic breast cancers but many limitations and resistances impair its efficacy. More importantly, Trastuzumab is not suited for treating the majority of breast cancers in which HER2 is weakly over-expressed. Here, the inventors report the design of a Fab-like bispecific antibody (HER2bsFab) that, by displaying a moderate affinity for HER2 antigen and a unique, specific and high FcγRIII-binding affinity, simultaneously and efficiently bound HER2-positive cells and NK cells. In vitro characterization showed that ADCC was the major mechanism of action of HER2bsFab as no significant HER2-driven effect was observed. A side by side comparison with Trastuzumab demonstrated a potent HER2bsFab-mediated ADCC at picomolar concentration against HER2$^{high}$ cells but also against Trastuzumab-refractive cell lines such as MCF-7 and JIMT-1 while sparing non-tumorigenic mammary epithelial cells. FcgammaRIIIA-engagement by HER2bsFab was independent of V158 polymorphism and induced, in all cases, a stronger NK cells activation in response to target cell recognition. In vivo studies in Nude mice demonstrated that HER2bsFab potently inhibited HER2$^{high}$ tumor growth by recruitment of FcgammaR-positive resident effector cells. Strikingly, HER2bsFab exhibited a net superiority over Trastuzumab at inhibiting HER2$^{low}$ tumor growth. Thus, taking advantage of its epitope specificity and affinity for HER2 and FcgammaRIIIA, HER2bsFab evades most of Trastuzumab Fc-linked limitations and decreases the threshold of HER2 density required to induce antitumor activity, thereby potentially enlarging the number of patients eligible for HER2 therapy.

As used herein the term "HER2" has its general meaning in the art and refers to the Human Epidermal Growth Factor Receptor 2 also known as Neu, ErbB-2, CD340 (cluster of differentiation 340) or p185. Amplification or over-expression of this gene has been shown to play an important role in the pathogenesis and progression of certain aggressive types of breast cancer.

As used herein the term "single domain antibody" has its general meaning in the art and refers to the single heavy chain variable domain of antibodies of the type that can be found in Camelid mammals which are naturally devoid of light chains. Such single domain antibody are also called VHH or "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388. The amino acid sequence and structure of a single domain antibody can be considered to be comprised of four framework regions or "FRs" which are referred to in the art and herein as "Framework region 1" or "FR1"; as "Framework region 2" or "FR2"; as "Framework region 3" or "FR3"; and as "Framework region 4" or "FR4" respectively; which framework regions are interrupted by three complementary determining regions or "CDRs", which are referred to in the art as "Complementarity Determining Region for "CDR1""; as "Complementarity Determining Region 2" or "CDR2" and as "Complementarity Determining Region 3" or "CDR3", respectively. Accordingly, the single domain antibody can be defined as an amino acid sequence with the general structure: FR1-CDR1-FR2-CDR2-FR3-CDR3-FR4 in which FR1 to FR4 refer to framework regions 1 to 4 respectively, and in which CDR1 to CDR3 refer to the complementarity determining regions 1 to 3. In the context of the invention, the amino acid residues of the single domain antibody are numbered according to the general numbering for VH domains given by the International ImMunoGeneTics information system aminoacid numbering (http://imgt.cines.fr/).

In particular, the present invention relates to an isolated single domain antibody comprising a CDR1 having least 70%, or at least 80%, or at least 90% of identity with sequence set forth as SEQ ID NO: 1, a CDR2 having at least 70%, or at least 80%, or at least 90% of identity with sequence set forth as SEQ ID NO:2 and a CDR3 having at least 70%, or at least 80%, or at least 90% of identity with sequence set forth as SEQ ID NO:3.

Amino acid sequence identity is preferably determined using a suitable sequence alignment algorithm and default parameters, such as BLAST P (Karlin and Altschul, Proc. Natl Acad. Sci. USA 87(6):2264-2268 (1990)).

In some embodiments the isolated single domain antibody according to the invention comprises a CDR1 having a sequence set forth as SEQ ID NO: 1, a CDR2 having a sequence set forth as SEQ ID NO:2 and a CDR3 having a sequence set forth as SEQ ID NO:3.

In some embodiments, the isolated single domain antibody according to the invention has the sequence set forth as SEQ ID NO:4.

In some embodiments, the single domain antibody is a "humanized" single domain antibody. As used herein the term "humanized" refers to a single domain antibody of the invention wherein an amino acid sequence that corresponds to the amino acid sequence of a naturally occurring VHH domain has been "humanized", i.e. by replacing one or more amino acid residues in the amino acid sequence of said naturally occurring VHH sequence (and in particular in the framework sequences) by one or more of the amino acid residues that occur at the corresponding position(s) in a VH domain from a conventional chain antibody from a human being. Methods for humanizing single domain antibodies are well known in the art. Typically, the humanizing substitutions should be chosen such that the resulting humanized single domain antibodies still retain the favourable properties of single domain antibodies of the invention. The one skilled in the art is able to determine and select suitable humanizing substitutions or suitable combinations of humanizing substitutions. For example, the single domain antibodies of the invention may be suitably humanized at any framework residue depicted in FIG. 6 provided that the single domain antibodies remain soluble and do not significantly loss their affinity for HER2 (Table 4).

A further aspect of the invention refers to a polypeptide comprising at least one single domain antibody of the invention.

Typically, the polypeptide of the invention comprises a single domain antibody of the invention, which is fused at its N terminal end, at its C terminal end, or both at its N terminal end and at its C terminal end to at least one further amino acid sequence, i.e. so as to provide a fusion protein. According to the invention the polypeptides that comprise a sole single domain antibody are referred to herein as "monovalent" polypeptides. Polypeptides that comprise or essentially consist of two or more single domain antibodies according to the invention are referred to herein as "multivalent" polypeptides.

In one embodiment, the polypeptide comprises at least one single domain antibody of the invention and at least one other binding unit (i.e. directed against another epitope, antigen, target, protein or polypeptide), which is preferably also a single domain antibody. Such a polypeptide is referred to herein as "multispecific" polypeptide; in opposition to a polypeptide comprising the same single domain antibodies ("monospecific" polypeptide). Thus, in some embodiments, the polypeptide of the invention may also provide at least one further binding site directed against any desired protein, polypeptide, antigen, antigenic determinant or epitope. Said binding site is directed against to the same protein, polypeptide, antigen, antigenic determinant or epitope for which the single domain antibody of the invention is directed agains, or may be directed against a different protein, polypeptide, antigen, antigenic determinant or epitope) from the single domain antibody of the invention. A "bispecific" polypeptide of the invention is a polypeptide that comprises at least one single domain antibody directed against a first antigen (i.e. HER2) and at least one further binding site directed against a second antigen (i.e. different from HER2), whereas a "trispecific" polypeptide of the invention is a polypeptide that comprises at least one single domain antibody directed against a first antigen (i.e. HER2), at least one further binding site directed against a second antigen (i.e. different from HER2) and at least one further binding site directed against a third antigen (i.e. different from both i.e. first and second antigen); etc.

In some embodiments, the further binding site is directed against an activating trigger molecule on an effector cell. Typically, said activating trigger molecule is selected from the group consisting of CD3, CD4, CD8, CD25, CD28, CD26, CTLA-4, ICOS, or CD11a. Other suitable antigens include but are not limited to those associated with immune cells including T cell-associated molecules, such as TCR/CD3 or CD2; NK cell-associated targets such as NKG2D, FcγRIIIa (CD16), CD38, CD44, CD56, or CD69; granulocyte-associated targets such as FcγRI (CD64), FcαRI (CD89), and CR3 (CD11b/CD18); monocyte/macrophage-associated targets (such as FcγRI (CD64), FcαRI (CD89), CD3 (CD11b/CD18), or mannose receptor; dendritic cell-associated targets such as FcγRI (CD64) or mannose receptor; and erythrocyte-associated targets such as CRI (CD35).

In some embodiments, the further binding site is directed against a serum protein so that the half-lie of the single domain antibody is increased. Typically, said serum protein is albumin.

Typically, the one or more further binding site may comprise one or more parts, fragments or domains of conventional chain antibodies (and in particular human antibodies) and/or of heavy chain antibodies. For example, a single domain antibody of the invention may be linked to a conventional (preferably human) VH or VL optionally via a linker sequence.

In one embodiment, the polypeptides comprise a single domain antibody of the invention that is linked to an immunoglobulin domain. For example the polypeptides comprise a single domain antibody of the invention that is linked to an Fc portion (such as a human Fc). Said Fc portion may be useful for increasing the half-life and even the production of the single domain antibody of the invention. For example the Fc portion can bind to serum proteins and thus increases the half life on the single domain antibody. In some embodiments, the at least one single domain antibody may also be linked to one or more (preferably human) CH1, and/or CH2 and/or CH3 domains, optionally via a linker sequence. For instance, a single domain antibody linked to a suitable CH1 domain could for example be used—together with suitable light chains—to generate antibody fragments/structures analogous to conventional Fab fragments or F(ab')2 fragments, but in which one or (in case of an F(ab')2 fragment) one or both of the conventional VH domains have been replaced by a single domain antibody of the invention. In some embodiments, one or more single domain antibodies of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more CH2 and/or CH3 domains of an antibody, such as from a heavy chain antibody and more preferably from a conventional human chain antibody; and/or may form and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid VHH domain or a humanized derivative thereof (i.e. a single domain antibody), in which the Camelidae CH2 and/or CH3 domain have been replaced by human CH2 and CH3 domains, so as to provide an immunoglobulin that consists of 2 heavy chains each comprising a single domain antibody and human CH2 and CH3 domains (but no CHI domain), which immunoglobulin has the effector function provided by the CH2 and CH3 domains and which immunoglobulin can function without the presence of any light chains.

In some embodiment, the polypeptide is as described in WO2006064136 and depicted in FIG. 1. In particular the polypeptide may consist of i) a first fusion protein wherein the CL constant domain of an antibody is fused by its N-terminal end to the C-terminal end to a single domain antibody according to the invention (i.e. a single antibody directed against HER2) and ii) a second fusion protein wherein the CH1 constant domain of an antibody is fused by its N-terminal end to the C-terminal end of a single domain antibody directed against an antigen different from HER2. In another particular embodiment, the polypeptide consists of a first fusion protein wherein the CH1 constant domain of an antibody is fused by its N-terminal end to the C-terminal end of a single domain antibody directed against a an activating trigger molecule on an effector cell (e.g. CD16) and a second fusion protein wherein the CL constant domain of an antibody is fused by its N-terminal end to the C-terminal end to a single domain antibody of the invention (i.e. HER2). Such a polypeptide is depicted in FIG. 1.

In specific embodiments, it is contemplated that the polypeptides of the invention used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 45 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the polypeptide of the invention described herein for therapeutic delivery.

According to the invention, the single domain antibodies and polypeptides of the invention may be produced by conventional automated peptide synthesis methods or by recombinant expression. General principles for designing and making proteins are well known to those of skill in the art.

The single domain antibodies and polypeptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. The single domain antibodies and polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors (Giga-Hama et al., 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC 12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In the recombinant production of the single domain antibodies and polypeptides of the invention, it would be necessary to employ vectors comprising polynucleotide molecules for encoding the single domain antibodies and polypeptides of the invention. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the protein of interest (e.g., a single domain antibody). Thus, a promoter nucleotide sequence is operably linked to a given DNA sequence if the promoter nucleotide sequence directs the transcription of the sequence.

The single domain antibodies and polypeptides of the invention are suitable for the treatment of HER2 positive cancers. Typically said cancer is selected from the group consisting of breast, colorectal, ovarian, pancreatic, lung, and urothelial cancers. In a particular embodiment, the single domain antibodies and polypeptides of the invention are suitable for the treatment of breast cancer. In some embodiments, the single domain antibodies and polypeptides of the invention are suitable for the treatment of a HER2 positive cancer in a patient for whom a treatment with Trastuzumab or Pertuzumab is not eligible. Typically, the patient is a HER2+ or HER2++ patient. Accordingly, in some embodiments, the present invention relates to a method for treating a HER2 positive cancer in a patient in need thereof comprising the steps consisting of i) staging the patient for its HER2 expression and ii) administering the patient with a single domain antibody or a polypeptide of the invention (e.g. a bispecific polypeptide) when the patient is considered at step i) as HER2+ or HER2++. Typically, testing is usually done at the same time as the initial biopsy or cancer surgery. Samples of cancer tissue from previous biopsies or an earlier surgery also may also be used. One skilled in the art can easily select the most appropriate method for staging the patient for its HER2 expression. Typically, the two main methods used for HER2 testing are immunohistochemistry (IHC) and fluorescence in-situ hybridization (FISH). 0-1+ means that a normal amount of the HER2 protein is present and the result is HER2-negative. 2+ means that a moderate amount of the HER2 protein is present. 3+ means that there is a higher than normal level of HER2 protein and the result is HER2-positive. By way of example, the method of the present invention typically comprise the step of i) determining the level of HER2 in tumor sample obtained from the patient, ii) comparing the level determined at step i) with a predetermined reference level and iii) administering the patient with a therapeutically effective amount of a single domain antibody or polypeptide of the present invention when the level determined at step i) is lower than the predetermined reference value.

According to the invention single domain antibody of the invention or the polypeptide of the invention is administered to the patient with a therapeutically effective amount.

By a "therapeutically effective amount" is meant a sufficient amount of the polypeptide (or the nucleic acid encoding for the polypeptide) to prevent for use in a method for the treatment of acute exacerbation of chronic obstructive pulmonary disease at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular patient will depend upon a variety of factors including the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The single domain antibodies and polypeptides of the invention (or the nucleic acid encoding thereof) may be combined with pharmaceutically acceptable excipients, and optionally sustained-release matrices, such as biodegradable polymers, to form pharmaceutical compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The polypeptide (or nucleic acid encoding thereof) can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The polypeptide (or nucleic acid encoding thereof) may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

The invention will be further illustrated by the following figures and examples. However, these examples and figures should not be interpreted in any way as limiting the scope of the present invention.

FIGURES

FIG. 1: Schematic representation of anti-HER2 antibody formats

Figure 2:
Figure 2:
Figure 2:
Figure 3:
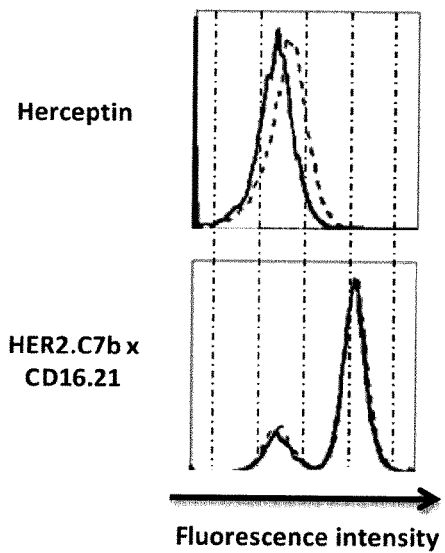

FIG. 2: Simultaneous recruitment of HER2$^{high}$ target cells and FcgRIIIA effector cells by bispecific HER2.C7BxCD16.21 bsFab FIG. 3: Competition assays demonstrating that FcγRIIIa binding by HER2.C7BxCD16.21 bsFab is not hindered by endogenous IgG FIG. 4: Effect of HER2 expression level on in vitro HER2.C7BxCD16.21 bsFab dependent cytotoxic activity FIG. 5: HER2.C7BxCD16.21 bsFab inhibits HER2$^{high}$ tumor growth in Nude mice.

FIG. 6 shows the C7B sequence (SEQ ID NO:4) aligned with human V region AJ879486 Homsap IGHV3-23*04 F (SEQ ID NO:13) and with human J region J00256 Homsap IGHJ4*01 (SEQ ID NO: 14) (http://imgt.cines.fr/). The framework residues that can be humanized appear in bold and underlined in the sequence.

EXAMPLE 1

Methods

Llama Immunization

A young adult male llama (*Lama glama*) was immunized subcutaneously at days 1, 30, 60, 90 and 120 with 50 million of HER2-expressing SK-OV-3 ovarian cancer cells. Sera were collected 15 days prior to each injection to follow the immune response against the immunogen.

VHH Library Construction

Blood samples were taken 15 days after each of the three latest immunizations and peripheral blood mononuclear cells were isolated by Ficoll-Histopaque-1077 (Sigma-Aldrich) discontinuous gradient centrifugation. Total RNA was isolated by acid guanidinium thiocyanate/phenol/chloroform extraction and synthesis of the cDNA was performed with Superscript II reverse transcriptase (GibcoBRL) using primer CH2FORTA4 (Arbabi Ghahroudi et al, *FEBS*, 1997). A first PCR was performed using an equimolar mixture of four backward primers originally designed to anneal on human VH genes (5' VH1-Sfi: 5'-CATGCCAT-GACTCGCGGCCCAGCCGGCCATGGCCCAGGTGCA-GCTGGTGCAGTCTGG-3'(SEQ ID NO:5); 5' VH2-Sfi: 5'-CATGCCATGACTCGCGGCCCAGCCGGCCATGGC-CCAGGTCACCTTGAAGGAGTCTGG-3' (SEQ ID NO:6); 5' VH3-Sfi: 5'-CATGCCATGACTCGCGGCCCA-GCCGGCCATGGCCGAGGTGCAGCTGGTG-GAGTCTGG-3' (SEQ ID NO:7); 5' VH4-Sfi: 5'-CATGC-CATGACTCGCGGCCCAGCCGGCCATGGCCCAGGT-GCAGCTGCAGGAGTCGGG-3'(SEQ ID NO:8)) and one forward primer (CH2FORTA4). These primers allow the amplification of two bands corresponding two the VH+CH1+hinge+part of CH2 gene fragment of traditional antibodies or the VHH+hinge+part of CH2 gene fragment of HcAbs. Using the gel-purified (Qiaquick gel extraction kit; Qiagen) lower band as the template, VHH genes were re-amplified using an equimolar mixture of the four backward primers (5' VH1 to 4-Sfi) and 3' VHH-Not primer (5'-CCACGATTCTGCGGCCGCTGAGGAGACRGT-GACCTGGGTCC-3') (SEQ ID NO:9) containing SfiI and NotI restriction enzyme sites. Resulting VHH fragments were purified from 1% agarose gel, digested with SfiI and NotI and ligated into pHEN1 phagemid (Hoogenboom et al, *Nucleic Acids Res,* 1991) digested with SfiI and NotI. The ligated material was transformed into TG1 *E. coli* electroporation-competent cells (Stratagen). Cells were plated on 2YT/ampicillin (100 μg/mL)/glucose (2%) agar plates. Colonies (106) were scraped from the plates with 2YT/ampicillin (100 μg/mL)/glucose (2%), and stored at −80° C. in the presence of 20% glycerol.

Selection of sdAb Anti HER2

Briefly, 10 μL of the library was grown in 50 mL of 2YT/ampicillin (100 μg/mL)/glucose (2%) at 37° C. to an OD$_{600}$ of 0.5. Five milliliters of the culture were then infected with 2·10$^{10}$ M13KO7 helper phage for 30 min at 37° C. without shaking. The culture was centrifuged for 10 min at 3000 g. The bacterial pellet was resuspended in 25 mL of 2YT/ampicillin (100 μg/mL)/kanamycine (25 μg/mL), and incubated for 16 h at 30° C. with shaking (270 rpm). The culture was then centrifuged for 20 min at 3000 g and one-fifth of the volume of 20% PEG 6000, 2.5 m NaCl was added to the supernatant and incubated for 1 h on ice to precipitate phage particles. The solution was then centrifuged for 15 min at 3000 g at 4° C. and the phage-containing pellet was re-suspended with 1 mL of NaCl/Pi. Phage were selected on purified recombinant HER2 ectodomain fused to a human Fc portion (10 μg/mL in NaCl/Pi for the first round of selection) or using 2×10$^6$ intact HER2-expressing SK-BR-3 cells (for the second round of selection). Antigens or cells were washed three times in PBS (by centrifugation step). Phage-sdAb library (1 mL) and antigens were saturated in milk PBS 2% during 2 h at room temperature or at 4° C. for cells. Phage-sdAb library was recovered and then incubated with antigens during 2 h at room temperature or at 4° C. for cells. Next, antigens or cells were washed ten times with 1 mL of PBS. Fixed phages were eluted with tryspin solution (Sigma) at 1 mg/mL during 30 min at room temperature with rotation. Eluted phages were resuspended with 200 µL NaCl/Pi and incubated without shaking with 1 mL of log-phase TG1 cells and plated on 2YT/ampicillin (100 µg/mL)/glucose (2%) in 243×243 mm dishes (Nalgene Nunc). Some isolated colonies were grown overnight in microtiter plate containing 200 µL 2YT/ampicillin (100 µg/mL)/glucose (2%) and stored at −80° C. after the addition of 15% glycerol (masterplates). The remaining colonies were harvested from the plates, suspended in 2 mL 2YT/ampicillin (100 µg/mL)/glucose (2%) and used for phage production.

ELISA Screening of Phage—sdAb

A 96-well plate replicator was used to replicate the masterplates in 120 µL of fresh broth. Colonies were grown for 2 h at 37° C. under shaking (400 rpm) and 35 µL 2YT/ampicillin (100 µg/mL)/glucose (2%) containing 2·10$^9$ M13K07 helper phage were added to each well and incubated for 30 min at 37° C. without shaking. The plate was centrifuged for 10 min at 1200 g and the bacterial pellet was suspended in 150 µL 2YT/ampicillin (100 µg/mL)/kanamycine (25 µg/mL) and grown for 16 h at 30° C. under shaking (400 rpm). Phage-containing supernatants were tested for binding to HER2-Fc by ELISA. Briefly, HER2-Fc was immobilized on magnetic epoxy beads (Dynabeads, Invitrogen) during 48 h at 4° C. following recommendation of the manufacturer. 2 µL of beads/well were used and blocked with 5% milk-PBS for 2 h at RT. Beads were washed and incubated for 1 h at RT with 50 µL of 2% milk-PBS containing phage supernatants. After 3 washes with PBS, beads with sdAbs were incubated with HRP-conjugated anti-M13 monoclonal antibody (GE Healthcare) in 2% milk-PBS for one hour at RT. After three washes in PBS, bound antibodies were detected using ABTS. Coloration was followed at 405 nm. After selection, 188 clones were screening and 92 clones were found positive by ELISA (data not shown). 20 clones were analyzed by sequencing, and all of them corresponded to a unique clone named HER2.C7b.

Construction of HER2×CD16 bsFab

HER2×CD16 bsFab was constructed by cloning the anti HER2 sdAb HER2.C7b in vector pBat14 (Rozan et al, MCT, 2012; WO2006/064136). Briefly, selected clone was amplified by two consecutive PCR using primers 3' VHHBsiWI Rev (3'-TGGTGCAGCCACCGTACGTGAGGAGACG-GTGACCTG-5') (SEQ ID NO:10) and 5' ICA1PCR1 (3'-CAGCTGGGTTATTATTGCTCGCTGCGCAGCCGGC-CATGGCCGAGGTGCAGCTGGTGCAG-5') (SEQ ID NO:11) for the first PCR and using primers 3' VHHBsiWI Rev and 5' EcoRIPCR2 (3'-ACAGGAAACAGAATTC-CATATGAAATACCTATTACCAACAGCAGCA-GCTGGGTTATTATTGC-5') (SEQ ID NO:12) for the second PCR. These two PCR allowed adding the two BsiWI and EcoRI sites. PCR fragments were cloned into the pBat14 vector between the BsiWI and EcoRI sites and purified. The resulting plasmid (pBat 271) allowed the expression of bsFab containing the sdAb HER2.C7b fused to the human Cκ domain and sdAb CD16.21 fused to the human CH1 domain. This bsFab was named HER2.C7b×CD16.21. All the constructions were sequence-verified.

Production and Purification of Antibodies

HER2.C7b×CD16.21 was purified from periplasm of E. coli DH5α. Bacteria were transformed with pBat271 plasmid and grown overnight in LB medium supplemented with 100 µg/ml ampicillin and 2% glucose. The starters were diluted in LB medium supplemented with 100 µg/ml ampicillin in order to reach an optical density of 0.1 and cultures were incubated at 30° C. When OD=0.8-0.9, the cultures were incubated 30 min at room temperature and the production was induced with 100 µM IPTG for 67 h at 20° C. Cells were harvested by centrifugation at 3700 g for 30 min at 4° C. and the cell pellet was resuspended in 4 ml cold TES buffer (0.2 M Tris-HCl, pH 8.0; 0.5 mM EDTA; 0.5 M sucrose) for 400 ml of supernatant, before adding 160 µl of lysozyme (10 mg/ml in TES buffer). Cells were subjected to an osmotic shock by adding 16 ml of cold TES diluted 1:2 with cold $H_2O$. After incubation for 30 min on ice, the supernatant was incubated with 25 µl DNase I (10 mg/ml) and $MgCl_2$ (10 mM final) for 30 min at room temperature. After another centrifugation step at 10,000 g, the supernatant was dialyzed against PBS 1×16 hours at 4° C. BsFab was purified by affinity chromatography from periplasmic extracts on IgG-CH1 matrix, followed by affinity chromatography on LC-kappa (Hu) matrix (Capture Select®, BAC BV). HER2.C7b×CD16.21 was finally concentrated on Vivaspin 10,000 (Millipore). Protein concentrations were determined using the DC Protein Assay (Bio-Rad Laboratories) according to manufacturer's instructions. Absorbance was measured in a Sunrise™ microplate absorbance reader (Tecan). BsFab purity and integrity were controlled by SDS-PAGE gel and western-blotting using mouse anti-his HRP mAb (Miltenyi biotec) and mouse anti-flag M2 mAb (Sigma Aldrich). An irrelevant bsFab targeted against mesothelin was produced and purified following exactly the same procedure. Soluble sdAb HER2.C7b was produced from the E. coli strain BL21 DE3. Briefly, an inoculum was grown overnight at 37° C. in 2YT medium supplemented with 100 mg/ml ampicillin and 2% glucose. Fresh 2YT medium supplemented with 2 mM $MgSO_4$, 0.05% glucose, 0.5% glycerol, 0.2% lactose and 100 mg/ml ampicillin was inoculated to obtain an $OD_{600\ nm}$ of 0.1. Bacteria were grown for 2 hours at 37° C. and then for 16 hours at 30° C. SdAb was purified by metal affinity chromatography as previously described. Sdab HER2.C7b-Fc was produced from culture supernatant of HEK293T cells. Briefly, cells were grown in DMEM medium supplemented with 10% IgG-stripped Fetal Bovine Serum (PAA Laboratories) one week before transfection. Then, they were transfected with the expression vector pHLsec aHER2.C7b-Fc (pBat229) using jetPEI reagent (Polyplus-transfection, France) according to the manufacturer's protocol. Twenty-four hours after transfection, medium was replaced and cells were incubated for another 48 hours. SdAb HER2.C7b-Fc was then purified from culture supernatants by Protein G affinity chromatography (Amersham Biosciences). Herceptin is a kind gift from Dr. D. Olive (CRCM, Marseille, France). The in vitro biotinylation of protein was performed using Ez-link micro NMHS-PEO4-biotinylation kit (Perbio science) following the recommendation of the manufacturer.

Target Cell Lines

The human ovarian adenocarcinoma SK-OV-3 (ATCC HTB-77) and the breast cancer cell lines SK-BR-3 (ATCC HTB-30), HCC1954 (ATCC CRL-2338) and BT-474 (ATCC HTB-20) were purchased from ATCC. The JIMT-1 (ACC 589) cell line was purchased from DSMZ. MDA-MB-231 was a kind gift of Dr. Marie Alix Poul (Paris, France). MCF7 was a kind gift of Dr. Daniel Olive (CRCM, Marseille, France). Jurkat-huFcγRIIIA/γ cells are Jurkat lymphoma T cells transfected with a cDNA encoding the extracellular domain of FcγRIIIA fused to the transmembrane and intracellular domains of the γ chain (gift of Prof. Eric Vivier, Marseille, France). Cell lines SK-BR-3, HCC1954 and BT-474 were cultured in RPMI+Glutamax-I (Invitrogen) complemented with 10% (v/v) fetal calf serum (PAA). Cell lines SK-OV-3, JIMT-1, MDA-MB-231 and MCF7 were cultured in DMEM+Glutamax-I (Invitrogen) complemented with 10% (v/v) fetal calf serum. Jurkat-huFcγRIIIA/γ cells were cultured in RPMI 1640+Glutamax-I medium supplemented with 10% FBS and 0.5 mg/ml of geneticin. All cell lines were grown in a humidified 37° C. incubator containing 5% $CO_2$. Cell number and viability were determined using a C-Chips Malassez counting chamber (PAA) after trypan blue staining (Invitrogen). All cell lines purchased from ATCC were not cultured for more than 2 months. Other cell lines used in this study have not been authenticated.

Isolation of Effector Cells

Human peripheral blood mononuclear cells (PBMCs) were isolated from fresh peripheral blood of healthy donors (Etablissement Francais du Sang, Marseille, France) by Ficoll LSM 1077 (PAA) gradient centrifugation. Cells were counted and by trypan blue staining and incubated overnight at 37° C. in RPMI 1640+Glutamax-I medium supplemented with 10% FBS at a concentration of $10^6$/ml. Untouched NK cells were isolated on an autoMACS Pro Separator (Miltenyi Biotec) by depleting non-NK cells using the NK cell isolation kit (Miltenyi Biotec) exactly as described by the manufacturer. NK number and viability were determined using a C-Chips Malassez counting chamber after trypan blue staining Affinity Determination $2\times10^5$ SK-BR-3 cells were incubated with various concentrations (from 500 nM to 0.05 nM) of either biotinylated HER2.C7b×CD16.21 or biotinylated sdAbs (HER2.C7b and HER2.C7b-Fc) for 2 hour at 4° C. After a washing step, bound antibodies were detected using PE-labeled streptavidin and analyzed by FACS. The inverse of the fluorescence was plotted as a function of the inverse of antibody concentration. $K_D$ was determined thanks to the equation: $1/(F-F_{back})=1/F_{max}+(K_D/F_{max})(1/[\text{antibody}])$ with F=fluorescence unit, $F_{back}$=background fluorescence and $F_{max}$ maximum of fluorescence.

Competition with Endogenous IgGs $2\times10^5$ Jurkat-huFcγRIIIA/γ cells were pre-incubated at 4° C. for 45 min with increasing concentrations of human serum (from 10% to 100%) followed by addition of a constant concentration of biotinylated bsFab HER2.C7b×CD16.21 (50 nM) or biotinylated Herceptin (200 nM), and further incubation for 45 min. After a washing step, bound antibodies were detected by FACS using PE-labeled streptavidin.

Rosette Forming Cell Assay

To determine whether HER2.C7b×CD16.21 can engage both CD16+ cells and HER2+ tumor cells, $5\times10^6$ SK-OV-3 cells were stained for 10 min at 37° C. with CellTrace™ CFSE (Invitrogen) at a final concentration of 20 µM in PBS 0.1% BSA. Reaction was stopped by adding cold PBS 0.1% BSA and cells were washed twice in RPMI 1640+Glutamax-I medium supplemented with 10% FBS. $5\times10^6$ Jurkat-huFcγRIIIA/γ were washed twice with RPMI 1640+Glutamax-I medium and stained for 30 min at 37° C. with CellTracker™ Red CMTPX (Invitrogen) at a final concentration of 100 µM. Cells were washed twice in RPMI 1640+Glutamax-I medium supplemented with 10% FBS and incubated and incubated in a large excess of medium for 30 min at 37° C. $25\times10^4$ Jurkat-huFcγRIIIA/γ and $5\times10^4$ SK-OV-3 cells were co-incubated for 2 hours at 37° C. in each well of a 24-well plate. Medium was then replaced by PBS 1% BSA supplemented with HER2.C7b×CD16.21 (40 nM), irrelevant bsFab (40 nM) or Herceptin (40 nM) at 37° C. during 4 hours. Rosette formation was observed by optical microscopy. Pictures were computerized analyzed using Adobe Photoshop CS3.

In Vitro Cytotoxicity Assays

Target cells ($5\times10^3$ cells/well) and effector cells (NKs) at constant E/T ratio (10/1) were coincubated in white flat-bottomed 96-well plates (Greiner) with either HER2.C7b× CD16.21 or Herceptin at different concentrations as indicated. NKs coincubated with tumor cells alone were used as controls. Following overnight incubation at 37° C., NKs were discarded by washing and target cell viability was quantified with Cell titer Glo viability assay according to manufacturer's protocol (Promega). Luminescence was measured in a Tristar LB941 microplate reader (Berthold Technologies), and raw data were analyzed in Excel XP (Microsoft). Percent cytotoxicity was calculated as follows: $[T-(T_{EAb}-E)]/[(T-(T_{dead}-E)]\times100$ with T=Target luminescent signal, E=effector luminescent signal, $T_{dead}$=luminescent signal of target lysed with 1% triton solution and $T_{EAb}$=Target+Effector+Antibody luminescent signal. Dose response curves were treated by non-linear regression analysis using Prism software (GraphPad Software). Data were expressed as mean±SD. All procedures were done in triplicate with different healthy donors.

In Vivo Efficacy in Xenografted Mice

Four-week-old female NMRI Nude mice (n=5/group) were purchased from Janvier Laboratories (France) and maintained in micro-isolator cages (4-6/cage) within a pathogen-free isolation facility with 12 light/dark cycle at 22 to 24° C. and 50% humidity. Animal care and use conformed to the French Animal Protection Law with the permission from the local authorities. To establish BT-474 or MCF7 xenograft models, mice were received implants of 60 day-release estrogen pellets (0.72 mg 17β-estradiol; Innovative Research of America). Two days after, mice were injected with $10\times10^6$ cells in 300 µL Matrigel/PBS (1:2 volume BD Matrigel Basement Membrane Matrix, BD Biosciences) s.c. in the right flank. To establish JIMT-1 xenograft model, mice were directly injected with $10\times10^6$ cells in 300 µL Matrigel/PBS (1:2 volume BD Matrigel Basement Membrane Matrix, BD Biosciences) s.c. in the right flank. All tumors were allowed to increase 150 to 250 mm³ size, and the mice were randomized into groups of 6 animals each. To test the efficacy of the bsFab on tumor growth inhibition, the mice were given HER2.C7b×CD16.21 i.p. by 5 mg/kg three times per week or Herceptin i.p. by 5 mg/kg twice a week. Negative control with the irrelevant bsFab targeted to mesothelin (5 mg/kg) was injected i.p. three times per week. The mice were followed for observation of xenograft growth rates, body weight and life spans. Tumor growth was measured with a Vernier caliper during 40 days to permit calculation of tumor volumes ($V=(L\times W^2)/2$, where L and W were length and width, respectively). At the end of experiment, all animals were sacrificed in accordance with institutional guidelines.

Flow Cytometry Assays

In all flow cytometry assays, fluorescence was measured using a MACSQuant (Miltenyi) and results were analyzed with the FlowJo software.

Statistical Analysis

Data from cytotoxicity assays are presented as mean±SD. Differences between groups were analyzed using Student's t test. Data from in vivo assays are presented as mean±SEM. Tumor size data were analyzed by ANOVA with post hoc Dunnett's test for comparison of treatment versus control group. Values of P<0.05 were considered significant. All data were plotted and analyzed using the GraphPad Prism software (GraphPad software).

EXAMPLE 2

Results

Construction of Bispecific HER2.C7bxCD16.21 Antibody:

The bispecific antibody (bsFab) HER2.C7bxCD16.21 consists of two covalently linked fusion proteins (FIG. 1). In the first one, a lama single domain antibody (sdAb) against the human HER2 receptor (HER2.C7b) is fused by its C-terminal end to the N-terminal end of the Ck constant domain of a human IgG1; in the second one, a sdAb against the human FcγRIII receptor (CD16.21) is fused by its C-terminal end to the N-terminal end of the CH1 domain of a human IgG1. The CH1 and Ck domains linked through a disulfide bond act as an heterodimerization motif. The cellular binding specificity of the bsFab was evaluated by flow cytometry on SK-BR-3 cells and on FcγRIIIa transfected Jurkat cells (data not shown). To allow direct comparison with HER2 engagement, a fusion protein (HER2.C7b-Fc) made of two HER2.C7b sdAb fused to the hinge, CH1 and CH2 domains of a human IgG1 was constructed. This molecule was thus bivalent for HER2 (FIG. 1).

Both molecules were produced in the periplasm of *E. coli* to allow a proper disulfide bond formation within each Ig domain and purified after periplasm extraction using a two-steps purification procedure, i.e. affinity chromatography on IgG-CH1 matrix, followed by affinity chromatography on LC-kappa (Hu) matrix.

Apparent Affinity of HER2.C7b Antibody Formats

The apparent affinity of biotinylated HER2.C7b sdAb, HER2.C7bxCD16.21 bsFab and HER2.C7b-Fc was determined by flow cytometry on SK-BR-3 cells (Table 1). As expected, the affinity of monovalent HER2.C7b (HER2.C7b sdAb and HER2.C7bxCD16.21 bsFab; 52 and 64 nM, respectively)) was lower than that of bivalent HER2.C7b (HER2.C7b-Fc); 3 nM).

Simultaneous Recruitment of HER2$^{high}$ Target Cells and FcγRIIIa Effector Cells by Bispecific HER2.C7bxCD16.21 bsFab The ability of HER2.C7bxCD16.21 bsFab to simultaneously recruit target cells (SK-BR-3) and effector cells (human FcγRIIIa transfected Jurkat) was demonstrated by co-culturing the cells in the presence of 40 nM HER2-C7bxCD16.21 bsFab, Herceptin or irrelevant bsFab (FIG. 2). The rosette formation was observed by optical microscopy. As shown in FIG. 2, rosettes were observed only in the presence of bsFab and Herceptin (red arrow: human FcγRIIIa transfected Jurkat; green arrow: SK-BR-3). In the insert, the same experiment was performed with CFSE stained SK-BR-3 cells and Red CMTPX stained FcγRIIIa+ Jurkat cells.

HER2.C7bxCD16.21 bsFab does not Compete with Endogenous IgGs for FcγRIIIA Binding It is well known that the binding of monoclonal antibodies on FcγRIIIa is impaired by the high amount of endogenous IgG in serum. The impact of serum IgG on FcγRIIIa binding by bsFab was analyzed by competition assay on FcγRIIIa-Jurkat cells. After a 45 min pre-incubation with 0% (filled grey), 20% (dashed line) and 100% (black line) human serum, the cells were incubated with biotinylated HER2-C7bxCD16.21 bsFab (50 nM) or biotinylated Herceptin (200 nM). After staining with PE-labeled streptavidin, the binding of antibodies on FcγRIIIa was analyzed by flow cytometry. In contrast to Herceptin, the binding of bsFab was not hindered by the presence of human IgG as demonstrated in FIG. 3. This result is in agreement with previous data showing that the epitope recognized by the CD16.21 sdAb is different from that recognized by the Fc fragment of IgG1.

HER2.C7bxCD16.21 bsFab Mediates Efficient In Vitro ADCC on Herceptin Insensitive Breast Cancer Cells.

Cell viability assays were performed to evaluate the capacity of bsFab to mediate the killing of breast cancer cells depending upon their HER2 expression profile: SK-BR-3, HCC 1954, and BT474 cells overexpress HER2; JIMT-1 cell, despite a relatively high HER2 expression level, remains insensitive to the Herceptin; finally, MDA-MB-231 and MCF-7 cells that show low or moderate HER2 expression level. In each case, Herceptin was used for comparison. Target cells were co-cultivated overnight with freshly purified human NK cells (E/T ratio: 1/10) in the presence of serial dilutions of either Herceptin or HER2.C7bxCD16.21 bsFab. Cell viability was quantified using the Cell Titer Glo viability assay (Promega). Percent cytotoxicity was calculated as follows: $[T-(T_{EAb}-E)]/[(T-(T_{dead}-E)]\times 100$ with T=Target cell signal, E=effector cell signal, $T_{dead}$=signal of target cells lysed with 1% triton solution and $T_{EAb}$=Target+Effector+Antibody signal.

Figure 4:
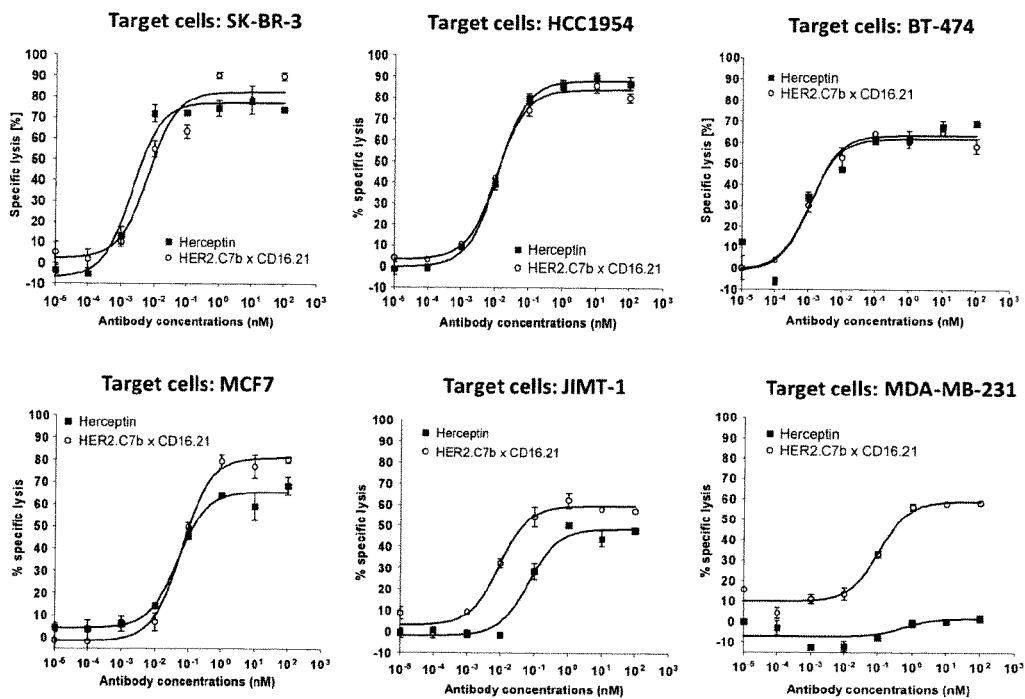

As shown in FIG. 4, Herceptin and bsFab displayed similar activities on HER2$^{high}$ cell lines (SK-BR-3, HCC 1954, BT-474) with similar $EC_{50}$ values and maximum lysis (Table 2). $EC_{50}$ values were still similar on MCF-7 cells, although the maximal lysis level obtained with the bsFab was slightly higher (74.5% versus 54%).

In the case of JIMT-1, HER2$^{high}$ but insensitive to Herceptin, the bsFab displayed a higher level of cytotoxicity (70% versus 50%) with an $EC_{50}$ value about 10-fold lower. The most striking effect was observed with the HER2$^{low}$ MDA-MB-231 cell line (usually considered as HER2 negative). While the cytotoxicity mediated by Herceptin was hardly measurable (maximum lysis ~16% and $EC_{50}$ not determined), HER2-C7bxCD16.21 bsFab remains able to mediate an efficient cytotoxicity as the maximal lysis induced by the bsFab reached 55% with a $EC_{50}$ value equal to 100 pM. Taken together these results demonstrate that HER2.C7bxCD16.21 bsFab is able to mediate in vitro an efficient cytotoxicity on cell lines insensitive to the Herceptin.

Inhibition of HER2$^{high}$ Tumor Growth by HER2.C7bxCD16.21 bsFab in Nude Mice

Figure 5A:
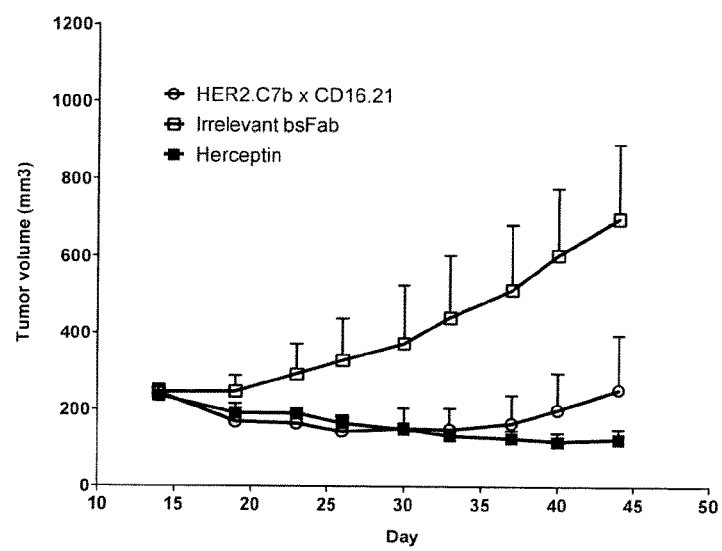

NMRI nude mice carrying an estrogen-release pellet were xenografted subcutaneously with 10 million of HER2$^{high}$ BT-474 cancer cells. When tumors reached a minimum size of ~200 mm$^3$, mice were treated i.p either with HER2.C7bxCD16.21 bsFab (5 mg/kg, 3 times per week), Herceptin (5 mg/kg, 2 times per week) or irrelevant bsFab (5 mg/kg, 3 times per week). Effect of these treatments on tumor growth was followed by caliper measurements twice a week. After 6 weeks of treatment, all control mice receiving irrelevant bsFab showed a continuous progression of tumor growth (FIG. 5A). As previously described in literature, Herceptin strongly inhibited tumor growth compared with control mice with a tumor growth inhibition rate of 96% ((mean tumor weight of the control group-mean tumor weight of the treatment group)/mean tumor weight of the control group)×100%).

Interestingly, mice treated with bsFab also showed a significant reduction of tumor progression compared with control group with a tumor growth inhibition rate of 60%.

No remarkable toxicity of the bsFab was observed as all treated animals survived throughout the experiment and showed a normal weight progression.

Figure 5B:
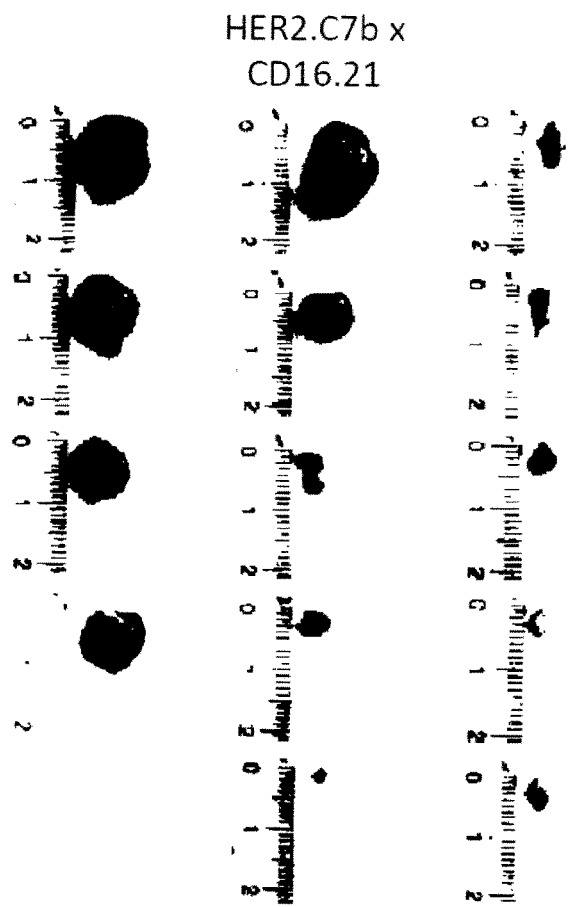

Representative tumor masses at week 6 are shown in FIG. 5B. Although differences in tumor sizes between control and treated mice were statistically significant, tumor masses from mice treated with HER2.C7bxCD16.21 bsFab appeared to be more heterogeneous than with Herceptin. This observation can explain the low tumor progression observed after 5 weeks (FIG. 5A).

TABLE 1

Apparent affinity of HER2.C7b antibody formats

|  | $K_d$ on HER2 (nM) |
| --- | --- |
| HER2.C7b | 51.6 |
| HER2.C7b-Fc | 2.9 |
| HER2.C7b × CD16.21 | 63.7 |

TABLE 2

Specific lysis and EC50 of bsFab and Herceptin dependent cytotoxicity

|  | bsFab HER2.C7b × CD16.21 | | Herceptin | |
| --- | --- | --- | --- | --- |
|  | EC50 (pM) | Specific lysis (%) | EC50 (pM) | Specific lysis (%) |
| SK-BR-3 | 3.3 | 76.3 | 2.3 | 77.4 |
| HCC1954 | 4.7 | 80.1 | 7.6 | 77.4 |
| BT-474 | 4.8 | 67.9 | 2.2 | 66 |
| JIMT-1 | 9.3 | 70 | 70 | 50 |
| MCF7 | 44 | 74.5 | 31.5 | 52 |
| MDA-MB-231 | 106 | 54.9 | ND | 15.9 |

TABLE 3

C7B sequence and its CDR:

| CDR1 | SEQ ID NO: 1 | GRTFSSYA |
| --- | --- | --- |
| CDR2 | SEQ ID NO: 2 | ISWSGANI |
| CDR3 | SEQ ID NO: 3 | AVKLGFAPVEERQYDY |
| C7B | SEQ ID NO: 4 | QVQLVQSGGGLVQAGGSLRLSCAASGRTFSSYAMAWFRQAPGKEREFVAAISWSGANIYVADSVKGRFTISRDNAKDTVYLQMNSLKPEDTAVYYCAVKLGFAPVEERQYDYWGQGTQVTVSS |

TABLE 4 list of the residues in SEQ ID NO: 4 that can be humanized.

| Residue | Position | Substitution |
| --- | --- | --- |
| Q | 1 | E |
| Q | 6 | E |
| A | 14 | P |
| A | 35 | S |
| F | 37 | V |
| E | 44 | G |
| R | 45 | L |
| F | 47 | V |
| A | 19 | S |
| V | 60 | Y |
| A | 75 | S |
| D | 77 | N |
| V | 79 | L |
| K | 87 | R |
| P | 88 | A |
| Q | 115 | L |

REFERENCES

Throughout this application, various references describe the state of the art to which this invention pertains. The disclosures of these references are hereby incorporated by reference into the present disclosure.

The invention claimed is:

1. A single domain antibody directed against human epidermal growth factor receptor 2 (HER2) comprising a CDR1 having a sequence set forth as SEQ ID NO: 1, a CDR2 having a sequence set forth as SEQ ID NO:2 and a CDR3 having a sequence set forth as SEQ ID NO:3.

2. The single domain antibody of claim 1 which is humanized.

3. A single domain antibody directed against human epidermal growth factor receptor 2 (HER2) which has a sequence set forth as SEQ ID NO:4.

4. The single domain antibody of claim 3 which is humanized.

5. A polypeptide comprising the single domain antibody according to claim 1.

6. The polypeptide of claim 5 further comprising a second single domain antibody against a second antigen that is different from HER2.

7. The polypeptide of claim 6 wherein the second single domain antibody is directed against an activating trigger molecule on an effector cell selected from the group consisting of CD3, CD4, CD8, CD25, CD28, CD26, CTLA-4, ICOS, CD11a, NKG2D, FcγRIIIa (CD16), CD38, CD44, CD56, CD69, FcγRI (CD64), FcγRI (CD89), CR3 (CD11b/CD18), FcγRI (CD64), FcγRI (CD89), CD3 (CD11b/CD18), mannose receptor, FcγRI (CD64) and mannose receptor, and CRI (CD35).

8. The polypeptide of claim 6 wherein the second single domain antibody is directed against CD16.

9. The polypeptide of claim 6 which comprises i) a first fusion protein wherein the CL constant domain of an antibody is fused by its N-terminal end to the C-terminal end of a single domain antibody according to claim 1 and ii) a second fusion protein wherein the CH1 constant domain of an antibody is fused by its N-terminal end to the C-terminal end of the second single domain antibody directed against an antigen different from HER2.

10. The polypeptide of claim 9 wherein the second single domain antibody is directed against CD16.

11. A polypeptide comprising the single domain antibody according to claim 3.

12. The polypeptide of claim 11 further comprising a second single domain antibody against a second antigen that is different from HER2.

13. The polypeptide of claim 12 wherein the second single domain antibody is directed against an activating trigger molecule on an effector cell selected from the group consisting of CD3, CD4, CD8, CD25, CD28, CD26, CTLA-4, ICOS, CD11a, NKG2D, FcγRIIIa (CD16), CD38, CD44, CD56, CD69, FcγRI (CD64), FcγRI (CD89), CR3 (CD11b/CD18), FcγRI (CD64), FcγRI (CD89), CD3 (CD11b/CD18), mannose receptor, FcγRI (CD64) and mannose receptor, and CRI (CD35).

14. The polypeptide of claim 12 wherein the second single domain antibody is directed against CD16.

15. The polypeptide of claim 6 which comprises i) a first fusion protein wherein the CL constant domain of an antibody is fused by its N-terminal end to the C-terminal end of a single domain antibody according to claim 1 and ii) a second fusion protein wherein the CH1 constant domain of an antibody is fused by its N-terminal end to the C-terminal end of the second single domain antibody directed against an antigen different from HER2.

16. The polypeptide of claim 15 wherein the second single domain antibody is directed against CD16.

* * * * *